(12) United States Patent
Sakalauskienė et al.

(10) Patent No.: US 11,723,584 B2
(45) Date of Patent: Aug. 15, 2023

(54) COMPLEX ANALYSIS SYSTEM OF SPECTROPHOTOMETRY AND ULTRASOUND IMAGES AND DATA FOR AUTOMATIC EARLY-STAGE DIAGNOSING OF MALIGNANT SKIN TUMORS

(71) Applicants: KAUNAS UNIVERSITY OF TECHNOLOGY, Kaunas (LT); LIETUVOS SVEIKATOS MOKSLŲ UNIVERSITETAS, Kaunas (LT)

(72) Inventors: Kristina Sakalauskienė, Kaunas (LT); Renaldas Raišutis, Kaunas (LT); Skaidra Valiukevičienė, Kaunas (LT); Gintarė Linkevičiūtė, Kaunas (LT)

(73) Assignees: KAUNAS UNIVERSITY OF TECHNOLOGY, Kaunas (LT); LIETUVOS SVEIKATOS MOKSLU UNIVERSITETAS, Kaunas (LT)

( * ) Notice: Subject to any disclaimer, the term of this patent is extended or adjusted under 35 U.S.C. 154(b) by 342 days.

(21) Appl. No.: 16/968,345

(22) PCT Filed: Feb. 4, 2019

(86) PCT No.: PCT/IB2019/050873
§ 371 (c)(1),
(2) Date: Aug. 7, 2020

(87) PCT Pub. No.: WO2019/155345
PCT Pub. Date: Aug. 15, 2019

(65) Prior Publication Data
US 2020/0390383 A1    Dec. 17, 2020

(30) Foreign Application Priority Data
Feb. 9, 2018    (LT) .................... LT2018 504

(51) Int. Cl.
A61B 5/00      (2006.01)
A61B 8/08      (2006.01)

(52) U.S. Cl.
CPC ............ *A61B 5/444* (2013.01); *A61B 5/0035* (2013.01); *A61B 5/0075* (2013.01); *A61B 5/443* (2013.01); *A61B 5/7264* (2013.01); *A61B 8/0858* (2013.01)

(58) Field of Classification Search
CPC combination set(s) only.
See application file for complete search history.

(56) References Cited

U.S. PATENT DOCUMENTS

| 6,238,342 B1 | 5/2001 | Feleppa et al. |
| 7,689,016 B2 | 3/2010 | Stoecker et al. |

(Continued)

FOREIGN PATENT DOCUMENTS

| WO | 2007020643 A2 | 2/2007 |
| WO | 2007020643 A3 | 4/2009 |

OTHER PUBLICATIONS

Bamber et al., "Combining High Frequency Ultrasound Reflex Transmission Imaging and Imaging Spectrophotometry for the Diagnosis of Skin Cancer". IEEE Ultrasonic Symposium, IEEE, Piscataway, NJ, USA. Oct. 2007, pp. 248-251. (Year: 2007).*

(Continued)

*Primary Examiner* — Yi-Shan Yang
(74) *Attorney, Agent, or Firm* — Nixon & Vanderhye

(57) ABSTRACT

Disclosed is a system and a method to analyze spectrophotometry and ultrasound images and data in a complex way to diagnose malignant skin tumors in early stages. The system consists of a high-frequency portable ultrasonic imaging device for in vivo skin examinations, an optical spectrophotometer with light sources of different wavelengths for skin chromophore registration, and a complex data processing algorithm providing an advisory diagnostic evaluation. This enables automatically aggregating data and (Continued)

quantitative estimates obtained by different imaging techniques for melanocyte-derived skin tumors, facilitating the decision support for acceptance of the final clinical diagnosis and treatment planning. The system allows simultaneous analysis of images recorded by devices with different physical principles, automatic separation of the tumor area and evaluation the depth of the tumor penetration into the superficial tissue, which is essential for the selection of further testing and treatment tactics, and the planning of surgical removal procedures.

1 Claim, 1 Drawing Sheet

(56) References Cited

U.S. PATENT DOCUMENTS

| 2004/0062056 A1 | 4/2004 | Heine et al. |
| 2006/0184024 A1 | 8/2006 | Da Silva et al. |
| 2008/0075340 A1 | 3/2008 | Cotton et al. |
| 2012/0321759 A1* | 12/2012 | Marinkovich ......... A61B 5/442 356/402 |
| 2017/0326385 A1* | 11/2017 | Fishman .............. A61N 5/1077 |

OTHER PUBLICATIONS

International Search Report for PCT/IB2019/050873 dated May 24, 2019, 3 pages.

Written Opinion of the ISA for PCT/IB2019/050873 dated May 24, 2019, 8 pages.

Bamber, J. et al., "Combining High Frequency Ultrasound Reflex Transmission Imaging and Imaging Spectrophotometry for the Diagnosis of Skin Cancer," 2007 IEEE Ultrasonics Symposium, pp. 248-251.

Yoshida, E. et al., "Spectrophotometer and ultrasound evaluation of late toxicity following breast-cancer radiotherapy," Med. Phys. 38 (10), Oct. 2011, pp. 5747-5755.

* cited by examiner

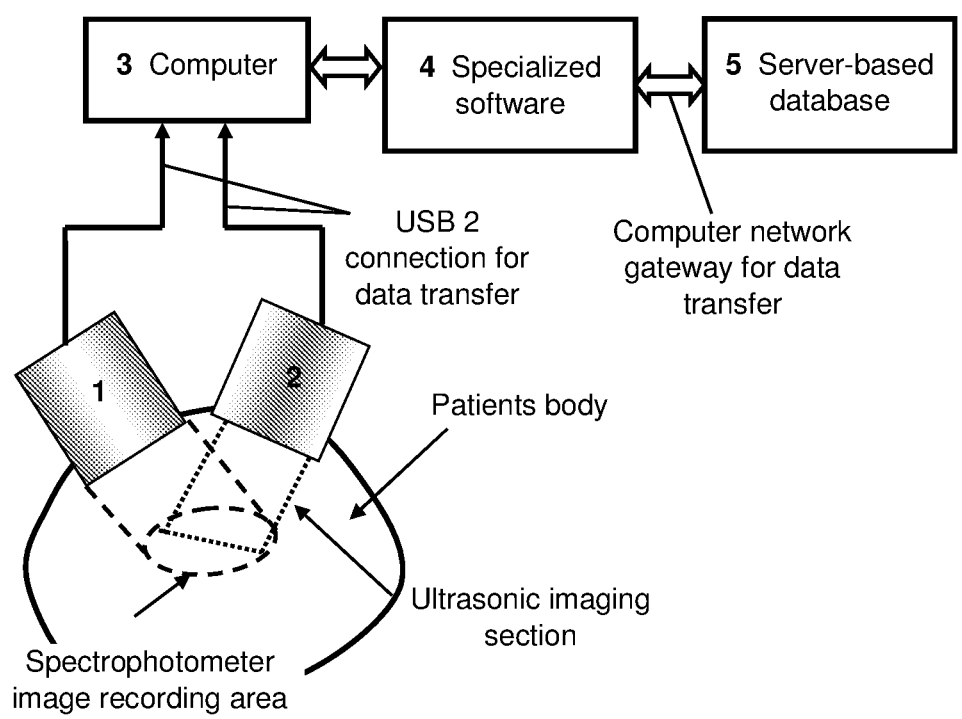

COMPLEX ANALYSIS SYSTEM OF SPECTROPHOTOMETRY AND ULTRASOUND IMAGES AND DATA FOR AUTOMATIC EARLY-STAGE DIAGNOSING OF MALIGNANT SKIN TUMORS

This application is the U.S. national phase of International Application No. PCT/IB2019/050873 filed Feb. 4, 2019 which designated the U.S. and claims priority to LT Patent Application No. LT2018 504 filed Feb. 9, 2018, the entire contents of each of which are hereby incorporated by reference.

FIELD OF THE INVENTION

The invention relates to the field of medical devices, and in particular to the spectrophotometry and ultrasound non-invasive diagnostic system and the method of complex analysis of images and data for the automatic early diagnosis of malignant skin tumors. This description provides a system and a method for non-invasive detection of human skin tumors (malignant or non-malignant).

STATE OF THE ART

The accuracy of clinical melanoma clinical diagnosis is only at 60% and strongly relies on the experience of the physician-dermatologist carrying out an analysis. The use of non-invasive imaging tools in clinical dermatology practice increases the accuracy of melanoma (malignant melanocyte-derived skin tumor) diagnosis by 10% to 27%. Dermatoscopes were the earliest devices used in dermatology. US 20040062056 A1 (date of publication 2004 Apr. 1) discloses a structure of a dermatoscope which has light emitting diodes set forth (arranged) around the optical magnification device illuminating the test area. Instead of many optical waveguides, one conical prism is used, which has light-emitting diodes on the base and whose cone angle is designed in such a way that the light spreads on the main surface from light-emitting diodes. Reflected and scattered light from the surface structures of the skin is visible to the eye.

Another non-invasive method of skin tumors imaging that was introduced in dermatology practice comparatively recently is spectrophotometric intracutaneous analysis. It is based on multispectral imaging of skin tumors by use of light sources of different wavelength: red, blue, green and infrared. Skin tissue chromophores (melanin, hemoglobin, and collagen) absorb light up to 2 mm in depth. US 2008075340 (date of publication 2008 Mar. 27) describes an image processing method and device for analysis of the spatial arrangement of surface tissue chromophores. The device described consists of a digital camera and an RGB image processing algorithm that displays a skin chromophore arrangement by creating an output image.

Computerized analysis and decision support information system is integrated in order to avoid any dependence on the investigator's experience. It automatically analyzes recorded optical images of pigment skin lesions and provides an estimation of malignancy.

Document U.S. Pat. No. 7,689,016 (date of publication 2010 Mar. 30) describes a computer analysis system based on quantification of skin tumor images recorded by dermatoscope and tumor classification.

WO 2007020643 A3 (date of publication 2009 Apr. 30) describes a device and a method to be used in the detection of pathological skin lesions by non-invasive way. An application of this method enables to find and identify different types of moles, tumors, lesions, and cancer diseases (melanoma) by a complex analysis of visible and infrared optical signals, on the basis of integral and spectral modes.

An assay of high-frequency (>20 MHz) ultrasound is used in dermatology to determine the thickness of the skin or skin pathology by in vivo conditions. US 20060184024 A1 (date of publication 2006 Aug. 17) describes a device for measuring tissue thickness based on ultrasonic wave transmission. The device consists of remote control and data processing units and manual ultrasonic transducer properly aligned with the tissues. A device for measuring muscle and fat tissue thickness records only one reflection signal. Document U.S. Pat. No. 6,238,342 B1 (date of publication 2001 May 29) describes an ultrasonic method and device for classification and visualization of different tissue types. The storage of clinical data, ultrasound radiofrequency (RD) data and the results of histological tests are included in the aforementioned document. Clinical and ultrasound RD data are provided as input variables for classifier training, which assigns the probability of cancer (a certain estimate) to each pixel on the ultrasound image. The probabilistic estimates of cancer are divided into ranges that can be set by the user when choosing threshold values. Different color or grayscale value is assigned to different ranges to distinguish suspicious areas in real time. This produces a parametric image corresponding to the actual ultrasound image. This can be useful for doctors in taking a biopsy to determine which area of tissue is most appropriate for taking the sample. Meanwhile, in the case of suspicion of melanoma, histological studies of skin tumors allow excising all tumors with certain determined reserve limits. If a histological examination reveals that the malignant tumor has not been removed radically, the removal should be repeated.

This description provides a system that automatically analyzes and evaluates skin tumor spectrophotometric images while recorded ultrasound data also provides a skin tumor malignancy rating by assigning it to one of the classes (benign or malignant).

The described skin non-invasive diagnostic solutions have the following disadvantages in comparison with the solution presented in this description:
  it is not possible to analyze data recorded by several different methods at the same time;
  only surface of tissues of skin tumor and their changes are evaluated by optical methods;
  the aforementioned systems do not evaluate the depth of penetration of the skin tumor into the superficial tissue.

This document describes the system and method for analyzing skin tumor data recorded by different physical imaging techniques of superficial tissue, for providing information on the expansion of tumor both on the surface and in depth of superficial tissues. An automatic system for evaluation of quantitative parameters and decision support information system contribute to the acceleration of a proper decision regarding diagnosis (malignant or non-malignant tumor), selection of follow-up tests, and planning treatment tactics.

SUMMARY OF THE INVENTION

The system and method for identifying malignant melanocyte-derived skin tumors, and more specifically, the system and method for assessing complex data on skin tumors recorded by spectrophotometry and ultrasound techniques, are described. The system consists of a high frequency (22 MHz) portable (operating via USB connection)

ultrasonic device for in vivo skin examination, an optical spectrophotometric device with different wavelength light sources (red, blue, green and infrared) for registration of resolution and spatial distribution of skin chromophore (melanin, hemoglobin and collagen), and the complex data processing algorithm, which provides a diagnostic estimate of a recommendatory nature (malignant or non-malignant skin tumor). The proposed technical solution makes the automatic aggregation (fusion) of data and quantitative estimation obtained for melanocyte-derived skin tumors by different imaging techniques possible; it facilitates the acceptance of the final clinical diagnosis and further planning of treatment tactics.

This description provides a system and a method to recognize human skin tumors (malignant or non-malignant) in a non-invasive way. The analysis system and method are for doctors of various specializations and/or other medical professionals who work with patients complaining of suspicious pigmented skin lesions. The system consists of a spectrophotometric intracutaneous analytical device and a high frequency (more than 20 MHz) ultrasonic imaging device that collects data from a two-dimensional section (B-type image); a personal computer used by a physician with specialized software and algorithm installed for image analysis, data analysis, automatic classifier and visualization. A database is accumulated to obtain the classification results, where the actual diagnosis of the injury is established during the histological examination of the section of the removed tumor. The data of the database is used for the training of the automatic tumor classifier (malignant or non-malignant) installed in specialized software. The study comprehensively evaluates images and data recorded by two non-invasive imaging techniques (spectrophotometric and ultrasonic) acting on different physical principles, and it is not limited to the strengths or weaknesses of any single method. The analysis is done automatically, it does not dependent on the examiner's experience, and can be used by an inexperienced dermatologist or therapist.

This system ensures the use of two methods (spectrophotometry (1) and ultrasound imaging (2)) for imaging of superficial tissue performed on the basis of two different physical principles for more informative skin tumor examination. An efficient examination of the skin tumor on the surface and in-depth (changes in the internal structure of the tissues) is provided by non-invasive and safe for a patient way (spectrophotometry (1) and ultrasound imaging (2)).

BRIEF DESCRIPTION OF THE FIGURES

In FIG. 1 a schematic diagram of the components of the spectrophotometric and ultrasound imaging and data analysis system is presented.

EMBODIMENTS

This description provides a system of complex analysis of spectrophotometry and ultrasound imaging and data for doctors of various specializations (e.g., dermatologists, plastic surgeons, therapists) and/or other medical professionals who work with patients complaining of suspiciously pigmented skin lesions. The system includes the following devices (FIG. 1):
  a spectrophotometric instrument for intracutaneous analysis (1);
  a high-frequency ultrasonic imaging device (2);
  a computer (3);
  specialized software for scanning and automatic analysis of recorded images and data (4).

In addition to the devices listed above, the system also includes a server-based database (5), where the data obtained by spectrophotometric and ultrasonic imaging devices is recorded, data for analysis can be read, and a quantitative parameter base for training of the automatic classifier is stored. Besides the listed devices, the system further includes the necessary technical means to ensure the interconnection of the devices for data exchange.

The camera of the spectrophotometric intracutaneous analysis device (1) (FIG. 1) is placed on the skin area to be examined on the patient, and dermatoscopic images, images of hemoglobin, collagen, epidermal and dermal melanin distribution in the skin are recorded. Cutaneous lesion to be examined should fit into the imaging window of the spectrophotometric device. If an incomplete image of the damage is recorded, the quantified parameters and the proposed malignancy estimate may be inaccurate. The camera of the spectrophotometric instrument must be immobilized (stable) during video recording; without proper recording of the lesion image, the test must be repeated. Recorded images are stored in the database (5). The histological examination data included into the server-based database (5), if possible, is used for the training of the automatic tumor classifier (malignant or non-malignant) installed in the specialized software (4) on the doctor's workstation computer.

High frequency (more than 20 MHz) ultrasonic imaging device (2) (FIG. 1) which operates with a single-element mechanical scanning ultrasonic transducer is used for visualization of deeper skin structures. The data is collected during mechanical scanning when the ultrasonic transducer is sliding orthogonally on the skin surface and recording information as 2D skin section view (B-type image). Before scanning, the ultrasonic transducer holder with a nozzle, that maintains a constant distance between the ultrasonic transducer and the skin (for the skin's surface to be in the focus area of the ultrasonic transducer) is pressed to the skin in such a way that the transducer's scanning axis would match with the maximum diameter of the skin lesion as much as possible. The holder of the transducer is filled with distilled water of room temperature. Scanning locates where the visually visible skin damage (tumor) is the deepest. When this location is found, the scan stops and the image and its data are stored in the database (5). The ultrasonic imaging device stores not only the image but also the raw radio-frequency reflected ultrasonic signals that can be loaded and processed to obtain more quantitative information about tissue area and tissue structure of interest. Recorded and stored skin lesion data are loaded and processed on a therapist's workstation computer (3) by the specialized software (4) and the algorithm that is capable of automatically processing of primary data, distinguishing, quantification and classification of the lesion. Clinical data, spectrophotometric images, ultrasound images and data, and histological results of the removed tumor are stored in the database and subsequently used for the classifier training to identify malignant skin tumors as accurately as possible.

The installed computer software (3) with image analysis, data analysis, automated classifier and image review algorithm (4) allows integration of the results obtained by different physical imaging techniques of superficial tissue (spectrophotometry (1) and ultrasound imaging (2)). This makes it possible to increase the comprehensiveness, reliability, and accuracy of the diagnosis of malignant tumors.

Using specialized software (4) and database (5), analysis of spectrophotometric and ultrasound imaging data is performed automatically; skin tumors are automatically classified as malignant and non-malignant, not depending on investigators experience, and can, therefore, be used by an inexperienced dermatologist or therapist.

Realization of an automatic skin tumor recognition algorithm implemented in specialized software (4) consists of the following key steps:

1. Loading of images recorded by a skin tumor spectrophotometer (1) and images and data recorded by an ultrasonic imaging device (2);

2. Distinguishing of tumor area by spectrophotometer (1) and ultrasound imaging device (2) in recorded images. During the separation of tumor area in the images recorded by spectrophotometer (1), the blue component of the dermatoscopic image is used to define the contour; the optimal threshold is determined using the Otsu method. Distinguishing of tumor area by the ultrasound imaging device (2) in the recorded data is performed using a local area spectral parameter of ultrasonic signal that has crossed the tumor area. The global threshold for parametric signals is used to set the limits;

3. Estimation of quantitative parameters is performed by using images recorded by spectrophotometer (1). More precisely, the parameterizing of the selected informative area of the image is performed, as well as the parameters of the surface shape of the tumor are evaluated. Spectral parameters of the contoured regions of tumor, tumor form parameters, and image texture parameters of the first and second range internal sections of the tumor are used for the parameterization of the data recorded by the ultrasonic imaging device (2);

4. Selection of informative parameters using the collected database (5);

5. Classification of tumors (malignant or non-malignant) using the automatic classification method with fixed weighting factors. In the specialized software (4), the results of the histological examination are read from the database (5), if possible, for the training of the automatic classification algorithm.

The invention claimed is:

1. A method, comprising the following steps:

recording first images, comprising dermatoscopic and individual skin chromophore spatial distribution images, by using a spectrophotometric device to emit light of different wavelengths onto an area of interest of skin;

recording second images and data, comprising B-mode images and data of the area of interest of the skin, using an ultrasonic imaging device operating at a frequency over 20 MHz for imaging structures beneath a surface of the skin;

compiling a database, including the first images, the second images and data, and histological data for classifying skin tumors;

classifying the area of interest of the skin using a computer processor that is configured to:
  load the first images recorded by the spectrophotometric device and the second images and data recorded by the ultrasonic imaging device,
  distinguish a tumor area in the first images recorded by the spectrophotometric device, wherein a blue component of the first images recorded by the spectrophotometric device is used to define the tumor area,
  determine a depth of the tumor area by the second images and data recorded by the ultrasonic imaging device,
  estimate quantitative parameters of the first images recorded by the spectrophotometric device, including each of parameterizing the first images and evaluating parameters of a surface shape of the tumor area, wherein spectral parameters of the tumor area, tumor form parameters, and image texture parameters of a first range and a second range of internal sections of the tumor area are used to parameterize the second images and data recorded by the ultrasonic imaging device, and
  use the estimated quantitative parameters and the database including the first images, the second images and data, and the histological data for classifying skin tumors, to classify and report the tumor area within the area of interest of the skin as one of a malignant tumor or a non-malignant tumor.

\* \* \* \* \*